(12) United States Patent
Taniguchi et al.

(10) Patent No.: US 12,357,190 B2
(45) Date of Patent: Jul. 15, 2025

(54) MAGNETIC RESONANCE IMAGING APPARATUS, IMAGE PROCESSING DEVICE, AND IMAGE PROCESSING METHOD

(71) Applicant: FUJIFILM Healthcare Corporation, Kashiwa (JP)

(72) Inventors: Yo Taniguchi, Chiba (JP); Tomoki Amemiya, Chiba (JP); Toru Shirai, Chiba (JP)

(73) Assignee: FUJIFILM Corporation, Tokyo (JP)

(*) Notice: Subject to any disclaimer, the term of this patent is extended or adjusted under 35 U.S.C. 154(b) by 35 days.

(21) Appl. No.: 18/379,393

(22) Filed: Oct. 12, 2023

(65) Prior Publication Data

US 2024/0138699 A1    May 2, 2024

(30) Foreign Application Priority Data

Oct. 27, 2022   (JP) ................ 2022-172696

(51) Int. Cl.
| | |
|---|---|
| *A61B 5/00* | (2006.01) |
| *A61B 5/02* | (2006.01) |
| *A61B 5/055* | (2006.01) |
| *G16H 30/40* | (2018.01) |

(52) U.S. Cl.
CPC .......... *A61B 5/055* (2013.01); *A61B 5/02007* (2013.01); *G16H 30/40* (2018.01)

(58) Field of Classification Search
None
See application file for complete search history.

(56) References Cited

U.S. PATENT DOCUMENTS

2018/0353098 A1* 12/2018 Ye .................. G01R 33/4818
2019/0250231 A1*  8/2019 Taniguchi .......... G01R 33/5618

FOREIGN PATENT DOCUMENTS

| | | |
|---|---|---|
| JP | 2011-024926 A | 2/2011 |
| JP | 6979151 B | 11/2021 |

* cited by examiner

*Primary Examiner* — Joel F Brutus
(74) *Attorney, Agent, or Firm* — Paul Teng (57) ABSTRACT

A technology is provided for stably synthesizing a blood vessel image while suppressing a decrease in brightness of a blood vessel in a case of synthesizing the blood vessel image. Optimization of an imaging parameter set for quantitative value map calculation is performed by adding at least one condition in which there is no decrease in brightness of a blood vessel in a region where no blood vessel is depicted in either an original image or a quantitative value image.

14 Claims, 10 Drawing Sheets

|     | T1 [ms] | T2 [ms] |
|-----|---------|---------|
| GM  | 1500    | 100     |
| WM  | 850     | 75      |
| fat | 300     | 70      |
| CSF | 3000    | 1200    |

MAGNETIC RESONANCE IMAGING APPARATUS, IMAGE PROCESSING DEVICE, AND IMAGE PROCESSING METHOD

CROSS-REFERENCE TO RELATED APPLICATION(S)

The present application claims priority from Japanese patent application 2022-172696 filed on Oct. 27, 2022, the content of which is hereby incorporated by reference into this application.

BACKGROUND OF THE INVENTION

1. Field of the Invention

The present invention relates to a magnetic resonance imaging technology, and more particularly, to a technology using a computed image to improve a blood vessel depiction capability in blood vessel imaging.

2. Description of the Related Art

Images obtained from a magnetic resonance imaging apparatus (hereinafter, referred to as an MRI apparatus) include an image reconstructed from a nuclear magnetic resonance signal (echo signal) as well as a quantitative value image (also referred to as a computed image) that is obtained by computing subject parameters and apparatus parameters for each pixel based on a plurality of images (original images) captured with different imaging parameters and using these parameters as pixel values.

The quantitative value image is obtained by using a signal function representing a relationship between a signal of the original image, and the subject parameters, the imaging parameters, and the apparatus parameters to perform a least-squares fit of the signal function for the imaging parameters of the plurality of original images and the pixel values thereof. Here, the imaging parameters include a repetition time, a setting intensity of a high-frequency magnetic field, a phase of the high-frequency magnetic field, and the like, the subject parameters include a longitudinal relaxation time T1, a transverse relaxation time T2, a spin density $\rho$, a resonance frequency f0, a diffusion coefficient D, a distribution of an irradiation intensity B1 of the high-frequency magnetic field, and the like, and the apparatus parameters include a magnetic field strength B0, a reception sensitivity distribution s, and the like.

There are several techniques for methods of creating quantitative value images, and for example, as one of the techniques for enabling simultaneous acquisition of computed images of a plurality of subject parameters and apparatus parameters, a method of estimating a quantitative value image (map) by constructing the signal function through numerical simulation has been proposed (JP2011-024926A).

Meanwhile, various magnetic resonance angiography (hereinafter, MRA) techniques have been developed for imaging blood vessels. As one of these techniques, there is a technique for obtaining a blood vessel image by synthesizing two or more types of MR images with different physical property values to be emphasized by using an optimized synthesis function to enhance brightness values of blood vessels (JP6979151B). JP6979151B has proposed using, as images to be synthesized, a computed image in which quantitative values such as T1, T2, and PD described above are used as pixel values, in addition to a T1-enhanced image and a PD image.

SUMMARY OF THE INVENTION

In the method of JP6979151B, an MRA image can be acquired by synthesizing images using synthesis parameters set for each divided region of the subject's tissue. However, in a case where the brightness of a partial region of the blood vessel is very small in all the original images to be used for the synthesis, the brightness of that region may still become small in the synthesized blood vessel image even when an optimized synthesis function is used to achieve uniform brightness in the blood vessel.

The present invention has been made in view of the above circumstances, and provides a technology for stably synthesizing a blood vessel image while suppressing a decrease in brightness of a blood vessel in a case of synthesizing the blood vessel image.

In the present invention, in generating a computed image to be used for synthesis of a blood vessel image, an imaging parameter set is optimized by adding a condition in which there is no decrease in brightness even in a partial region of the blood vessel with small brightness.

Specifically, according to the present invention, there is provided an MRI apparatus comprising: a measurement unit configured to apply a high-frequency magnetic field and a gradient magnetic field to a subject placed in a static magnetic field to measure an echo signal generated from the subject in accordance with a predetermined imaging condition and a predetermined imaging sequence; an image reconstruction unit configured to create a reconstructed image from the measured echo signal; an imaging condition determination unit configured to determine combinations of a plurality of imaging conditions having different combinations; a quantitative value image generation unit configured to use a plurality of the reconstructed images created by the image reconstruction unit from respective echo signals acquired with the plurality of imaging conditions and a signal function determined by the imaging sequence to generate a quantitative value image in which a quantitative value related to the subject is used as a pixel value; and a synthetic image generation unit configured to synthesize a blood vessel image by synthesizing a part or an entirety of an original image including the reconstructed image and the quantitative value image. The imaging condition determination unit is configured to incorporate at least one imaging condition in which a local decrease in brightness of a blood vessel is small, into the combinations of the plurality of imaging conditions.

According to the present invention, in a case of determining imaging parameters, it is ensured that there is always brightness in any one of the images to be used for synthesis in all regions of the blood vessel. Therefore, this eliminates the decrease in brightness of a part of the blood vessel in the synthesized blood vessel image. As a result, a synthetic blood vessel image can be stably acquired.

BRIEF DESCRIPTION OF THE DRAWINGS

FIGS. 5A and 5B are diagrams showing a sequence diagram in the embodiment of the present invention, in which

DESCRIPTION OF THE PREFERRED EMBODIMENTS

Hereinafter, an embodiment to which the present invention is applied will be described. In the following description, imaging conditions include parameters (also referred to as imaging parameters) that can be arbitrarily set by a user during execution of an imaging sequence. In some cases, an imaging pulse sequence itself is also included in the imaging conditions. Further, parameters dependent on the subject are called subject parameters, and parameters unique to an MRI apparatus are called apparatus parameters.

The imaging conditions (imaging parameters) include, for example, a repetition time (TR), an echo time (TE), a setting intensity (flip angle: FA) of a high-frequency magnetic field, a phase (θ) of the high-frequency magnetic field, and the like. The subject parameters include a longitudinal relaxation time (T1), a transverse relaxation time (T2), a spin density (ρ), a resonance frequency difference (Δf0), a diffusion coefficient (b), an irradiation intensity distribution (B1) of the high-frequency magnetic field, and the like. The apparatus parameters include a static magnetic field intensity (B0), a sensitivity distribution (Sc) of a reception coil, and the like. The resonance frequency difference Δf0 is a difference between the resonance frequency of each pixel and the reference frequency f0.

First, an embodiment of the MRI apparatus according to the present invention will be described with reference to FIG. 1. In all the drawings illustrating the embodiment of the present invention, components having the same function are designated by the same reference numerals, and the description thereof will not be repeated.

Figure 1:
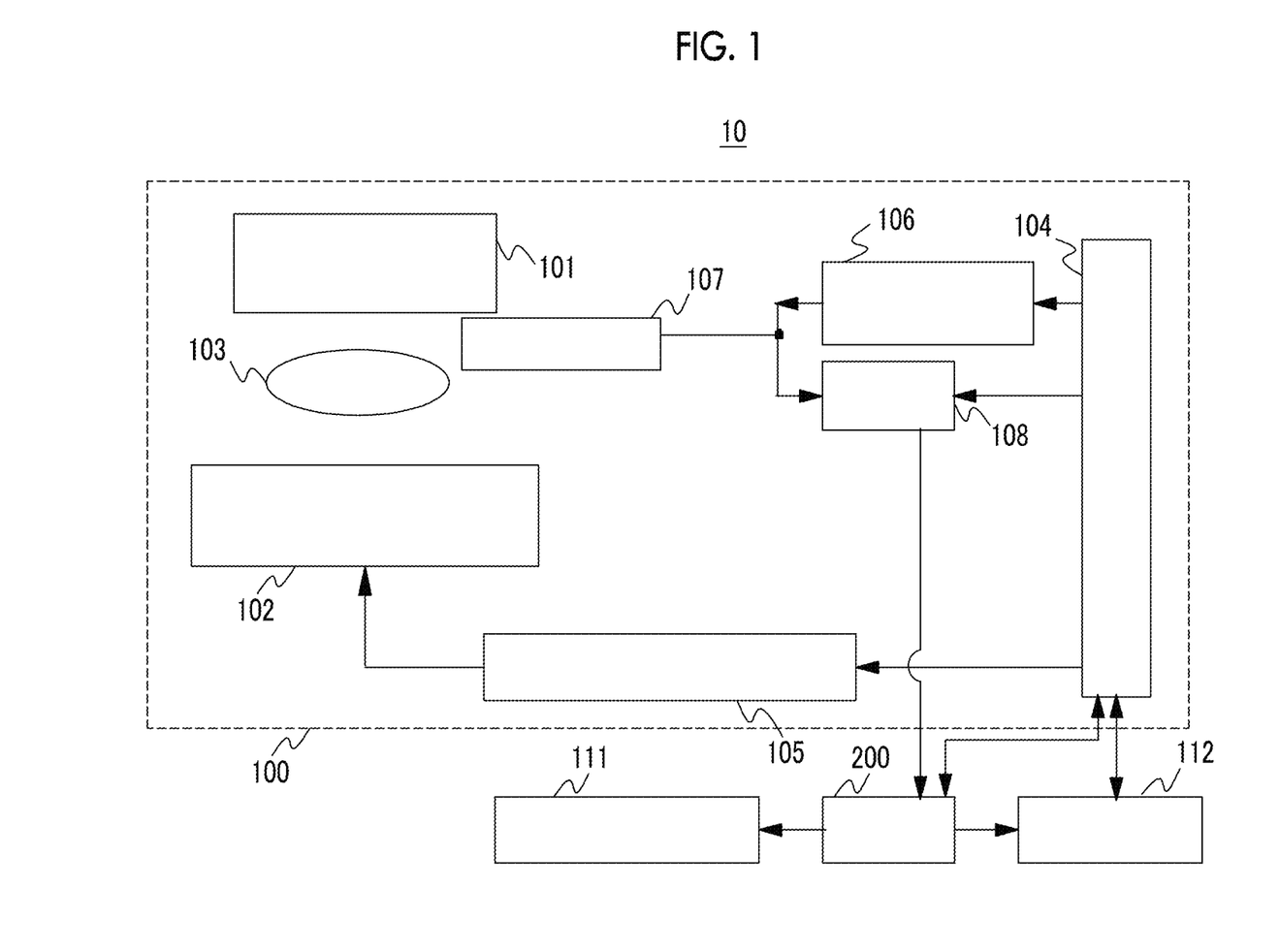
FIG. 1 is a block diagram showing a schematic configuration of an MRI apparatus of an embodiment of the present invention.

FIG. 1 is a block diagram showing a schematic configuration of an MRI apparatus 10 of the present embodiment. The MRI apparatus 10 comprises, as a measurement unit 100 that measures an echo signal, a static magnetic field-generating magnet 101, a gradient magnetic field coil 102 for generating a gradient magnetic field, a sequencer 104, a gradient magnetic field power supply 105, a high-frequency magnetic field generator 106, a transmission/reception coil 107 for emitting a high-frequency magnetic field and detecting a nuclear magnetic resonance signal, and a receiver 108. In addition, a computer 200 that performs various computational operations such as control of the measurement unit 100 and image reconstruction using the measured echo signal and the like, a display 111, and a storage medium 112 are provided. Although a single transmission/reception coil 107 is shown in the drawing, a transmission coil and a reception coil may be provided separately.

A subject (for example, a living body) 103 is placed on a bed (table) within a space of the static magnetic field generated by the magnet 101.

The sequencer 104 sends commands to the gradient magnetic field power supply 105 and the high-frequency magnetic field generator 106 to generate the gradient magnetic field and the high-frequency magnetic field, respectively. The high-frequency magnetic field is applied to the subject 103 through the transmission/reception coil 107. The nuclear magnetic resonance signal generated from the subject 103 is received by the transmission/reception coil 107 and is detected by the receiver 108. The nuclear magnetic resonance frequency (detection reference frequency f0) to be used as a detection reference is set by the sequencer 104. The sequencer 104 usually performs control such that each device operates at a timing and an intensity programmed in advance. Among programs, a program that particularly describes the high-frequency magnetic field, the gradient magnetic field, and the timing and the intensity of signal reception is called a pulse sequence (imaging sequence).

The computer 200 controls the measurement unit via the sequencer 104 and performs processing such as image reconstruction by receiving the signal detected by the receiver 108. The result is displayed on the display 111. The storage medium 112 can also store the detected signal and imaging conditions as necessary.

The processing performed by the computer 200 of the present embodiment includes, as processing specialized for blood vessel imaging, processing of generating a quantitative value image and synthesizing the quantitative value image and the reconstructed image to generate a synthetic blood vessel image.

Figure 2:
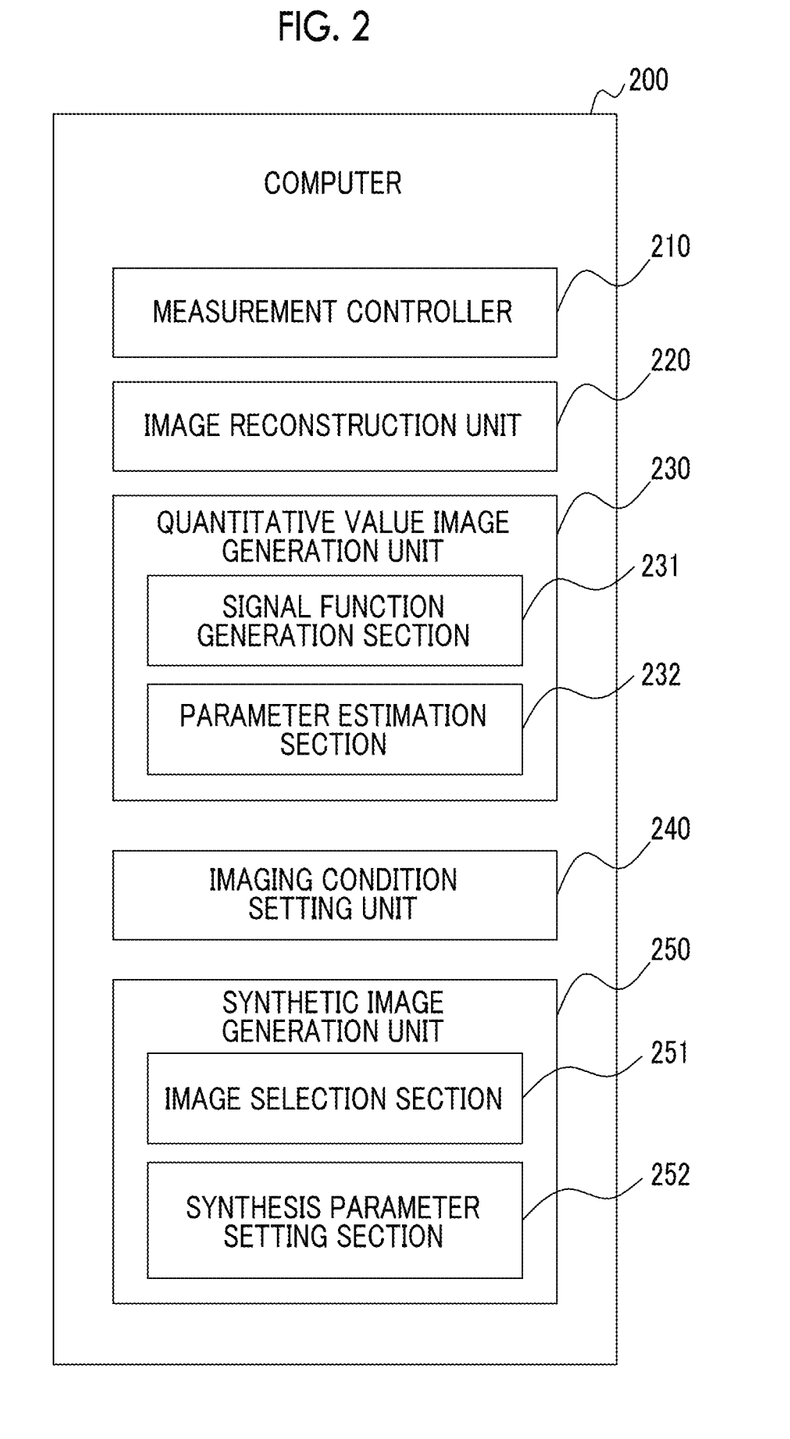
FIG. 2 is a functional block diagram of a computer according to the embodiment of the present invention.

In order to achieve the processing, as shown in FIG. 2, the computer 200 of the present embodiment comprises a measurement controller 210 that controls the measurement unit 100, an image reconstruction unit 220 that obtains the reconstructed image from the measured echo signal, a quantitative value image generation unit 230 that generates the quantitative value image using the reconstructed images acquired with combinations of a plurality of different imaging conditions, an imaging condition determination unit 240 that determines a plurality of imaging conditions for generating the quantitative value image, and a synthetic image generation unit 250 that generates a synthetic image by synthesizing at least two or more original images including the reconstructed image and the quantitative value image.

Further, the quantitative value image generation unit 230 may comprise a signal function generation section 231 that generates a signal function for estimating a parameter that is a quantitative value, a parameter estimation section 232, and the like. The quantitative value is at least one of parameters dependent on the subject or parameters unique to the apparatus, and a quantitative value for each pixel is obtained. A distribution (map) of the quantitative value obtained for each pixel is the quantitative value image. In addition, the synthetic image generation unit 250 may comprise an image selection section 251 that selects a plurality of original images and a synthesis parameter setting section 252 that sets parameters for the synthesis function.

Figure 3:
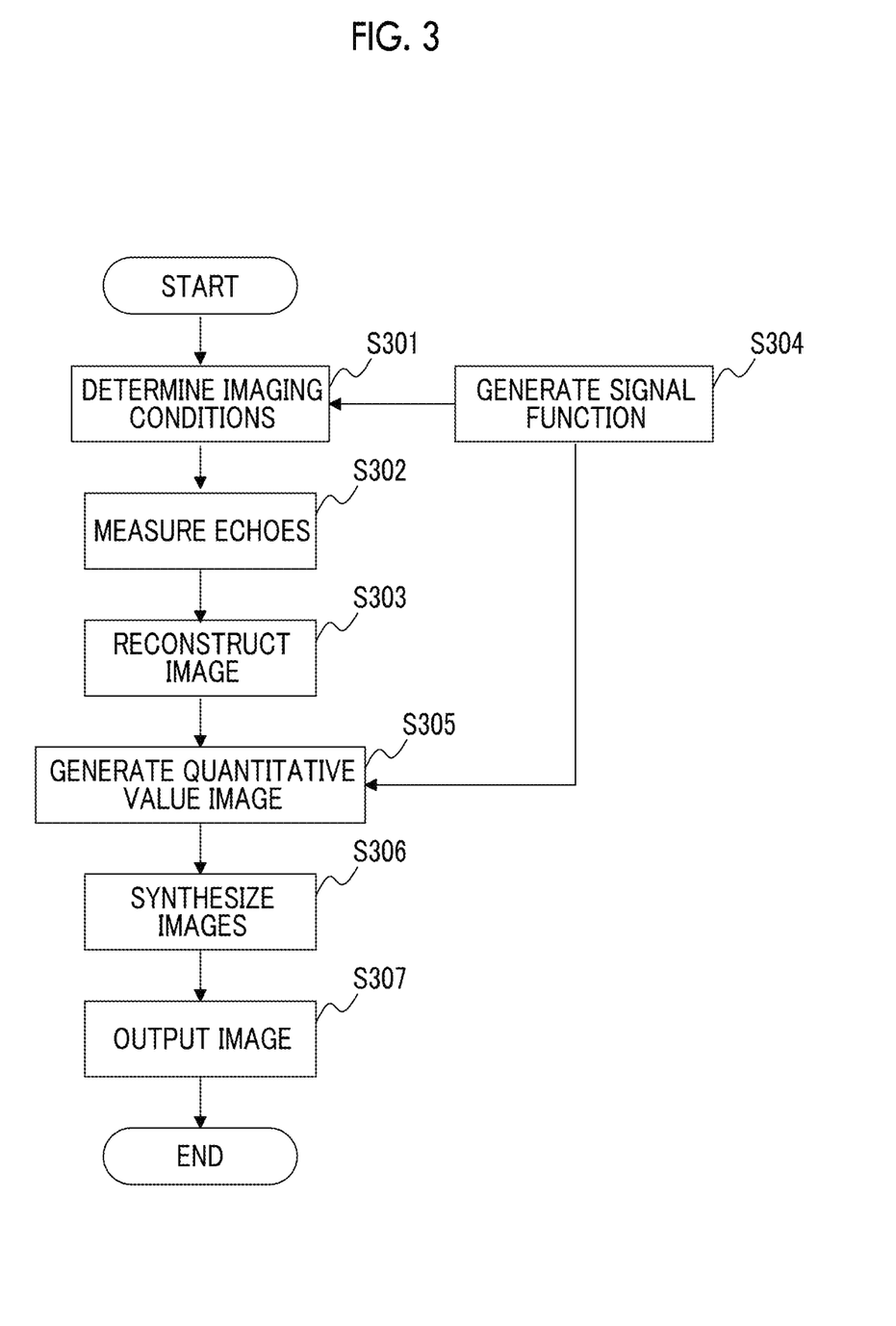
FIG. 3 is a processing flow in the embodiment of the present invention.

In the above configuration, as shown in FIG. 3, the measurement controller 210 controls the measurement unit 100 and the image reconstruction unit 220 based on combinations of the plurality of imaging conditions determined by the imaging condition determination unit 240 (S301) and obtains a plurality of reconstructed images with different combinations of the imaging conditions (S302 and S303). The quantitative value image generation unit 230 generates the quantitative value image using the plurality of reconstructed images. For example, the signal function generation section 231 generates a signal function for each imaging sequence through numerical simulation (S304), and the parameter estimation section 232 estimates the subject parameter for each pixel using the signal function for each imaging sequence, obtains a subject parameter distribution, and generates the quantitative value image of the subject from the subject parameter distribution (S305).

The synthetic image generation unit 250 synthesizes two or more types of original images consisting of the quantitative value image and the plurality of reconstructed images using a predetermined synthesis function (S306). As the synthesis function and its parameters (synthesis parameters) to be used for the synthesis, predetermined synthesis function and parameters may be used, or the synthesis parameter setting section 252 may set optimized synthesis function and parameters. The synthetic blood vessel image generated by the synthetic image generation unit 250 is displayed on the display 111 (S307).

Such functions of the computer 200 are implemented by loading and executing the programs stored in the storage medium 112 into the memory by a CPU of the computer 200. In addition, the functions may be implemented by hardware such as a programmable logic device (PLC). Note that all or some of the functions of the quantitative value image generation unit 230 and the synthetic image generation unit 250 may be implemented in a computer (an image processing device) which is a computer (an image processing device) provided independently of the MRI apparatus 10 and capable of data transmission and reception with the computer 200 of the MRI apparatus 10.

Figure 4:
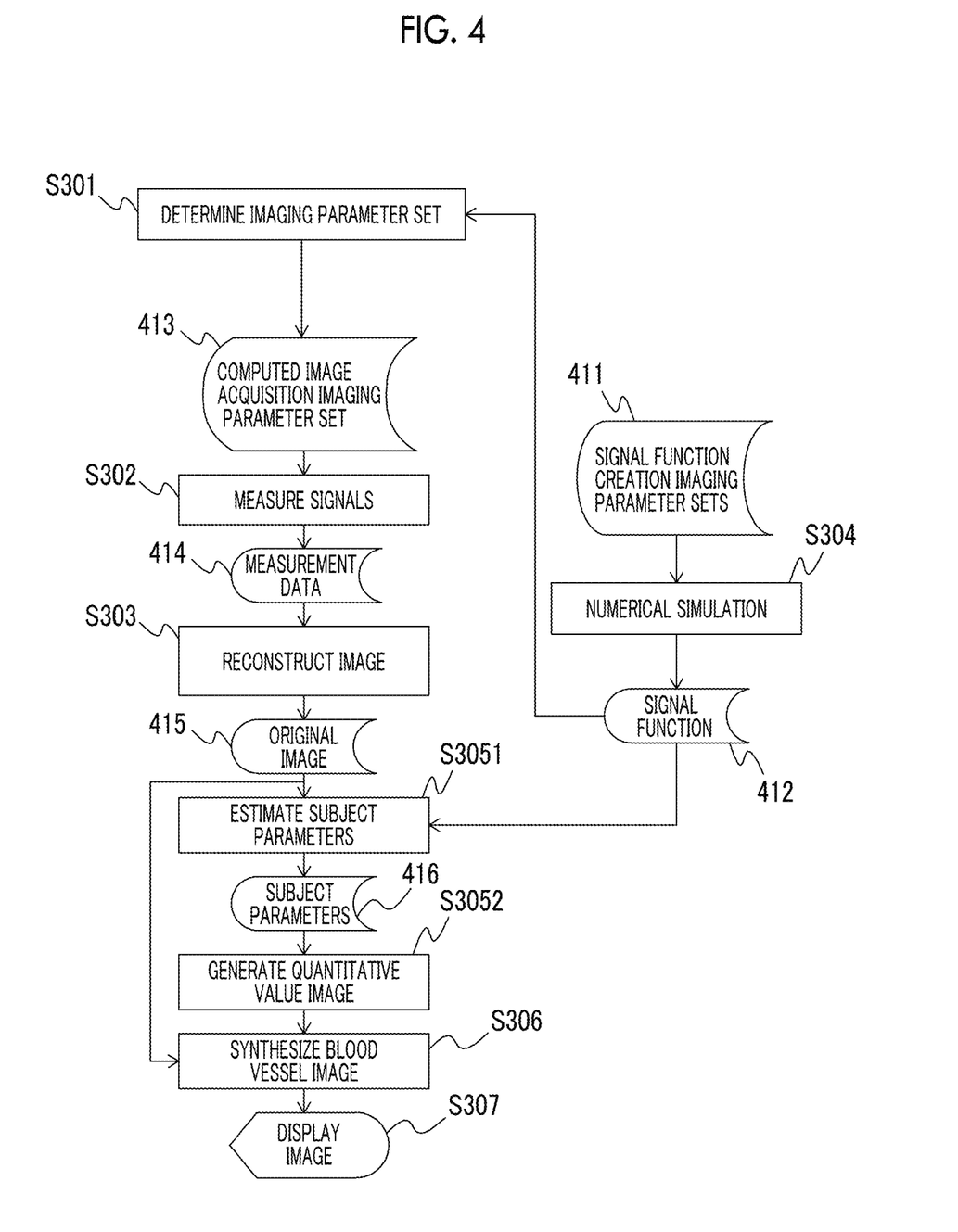
FIG. 4 is a flowchart showing details of processing of FIG. 3.

Hereinafter, specific contents of the processing within the computer 200 in the blood vessel imaging will be described with reference to FIG. 4. FIG. 4 is a diagram showing the processing of FIG. 3 in detail, and steps having the same processing contents as those of FIG. 3 are indicated by the same reference numerals.

Figure 5A:
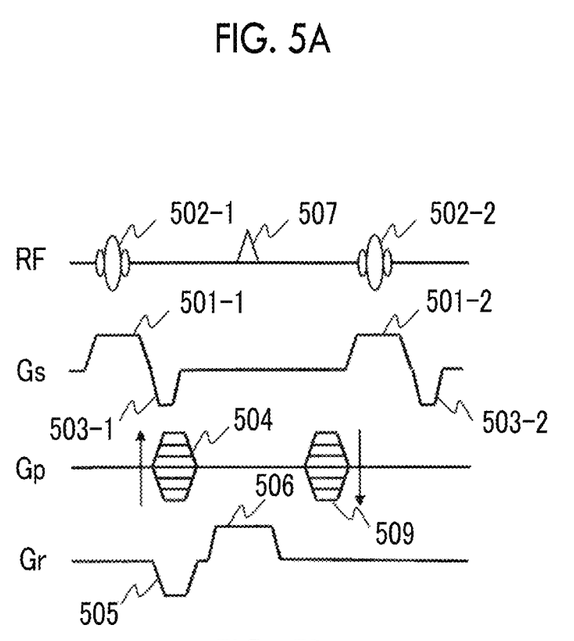
FIG. 5A is a diagram showing a general gradient echo-based pulse sequence.
Figure 5B:
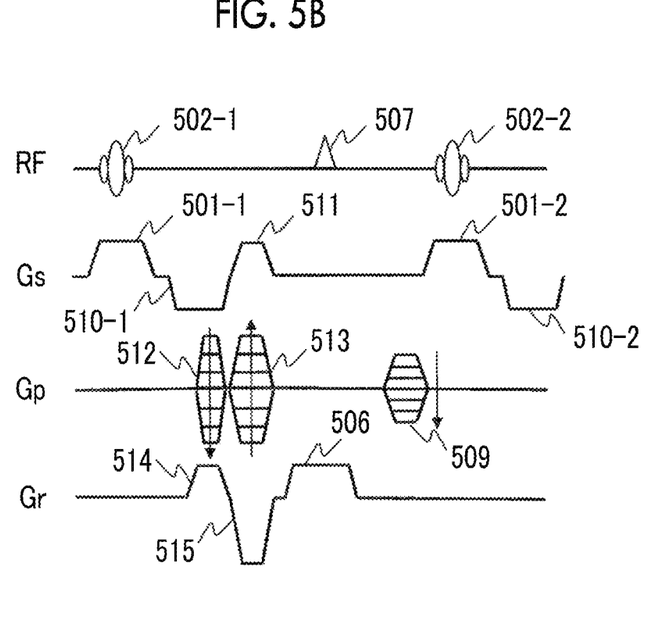
FIG. 5B is a diagram showing a gradient echo-based pulse sequence to which a flow compensation pulse is added.

Here, as an example, a case of using a GE type RF-spoiled GE sequence (hereinafter, abbreviated as an RF-spoiled GE) shown in FIG. 5A as the imaging sequence will be described. In FIGS. 5A and 5B, RF, Gs, Gp, and Gr represent a high-frequency magnetic field, a slice gradient magnetic field, a phase-encoding gradient magnetic field, and a readout gradient magnetic field, respectively. The "-1" and "-2" such as "501-1" and "501-2" are signs for distinguishing the same pulse for each repetition.

In this pulse sequence, first, a high-frequency magnetic field (RF) pulse 502 is emitted together with the application of a slice gradient magnetic field pulse 501 to excite the magnetization of a certain slice within a target object. Next, after applying a slice re-phase gradient magnetic field pulse 503, a phase-encoding gradient magnetic field pulse 504 for adding positional information in a phase-encoding direction to the magnetization phase, and a readout gradient magnetic field 505 for dephasing, a magnetic resonance signal (echo) 507 is measured while applying a readout gradient magnetic field pulse 506 for adding positional information in a readout direction. Finally, a phase-encoding gradient magnetic field pulse 509 for dephasing is applied.

The procedures described above are repeated at a repetition time TR while changing the intensities (phase-encoding amounts kp) of the phase-encoding gradient magnetic field pulses 504 and 509 and changing the phase increment value of the RF pulse by 117 degrees (the phase of n-th RF pulse is $\theta(n)=\theta(n-1)+117n$), and echoes necessary for obtaining one image are measured.

In the RF-spoiled GE, an image in which T1 (longitudinal relaxation time) is enhanced is obtained.

Generation of Signal Function: S304

The signal function generation section 231 generates the signal function to be used to determine the imaging conditions (S301). In the present embodiment, a signal function 412 of the RF-spoiled GE is created through numerical simulation. A signal function fs of the RF-spoiled GE is represented by Equation (1).

$$I=\mathrm{fs}(\rho,T1,T2,B1,\mathrm{FA},\mathrm{TR},\mathrm{TE},\theta,\mathrm{Sc})=\rho \mathrm{Sc}(T1,T2,B1\times\mathrm{FA},\theta,\mathrm{TR},\mathrm{TE}) \quad (1)$$

Here, T1, T2, $\rho$, and B1 are the longitudinal relaxation time, the transverse relaxation time, the spin density, and the RF irradiation intensity of the subject parameters, respectively. In addition, Sc is the reception coil sensitivity of the apparatus parameter. Since B1 is a coefficient of a flip angle (FA) during imaging, it is expressed as a product with FA. Since $\rho$ and Sc act as proportional coefficients with respect to the signal intensity, $\rho$ and Sc are factored outside the function.

The imaging parameters that can be changed in this RF-spoiled GE are the flip angle (FA), the repetition time (TR), the echo time (TE), and the RF phase increment value ($\theta$). Among these, the RF phase increment value is generally fixed at 117 degrees such that an image contrast with less T2 dependence equivalent to fast low-angle shot (FLASH), which is one of high-speed imaging methods, is obtained. In a case where this $\theta$ is changed, the T2 dependence of the image contrast changes significantly.

In the numerical simulation, signals are created by comprehensively changing the imaging parameters FA, TR, and $\theta$ for any values of T1 and T2 of the subject parameters, and the signal function is created using interpolation. It is assumed that the spin density $\rho$, B1, and Sc of the imaging target are constant (for example, 1).

The imaging parameter and the subject parameter are changed as follows, for example. The parameters are changed to include the ranges of imaging parameters to be used for actual imaging and the ranges of T1 and T2 of the subject, respectively.

4 values of TR [ms]: 10, 20, 30, 40
10 values of FA [degrees]: 5, 10, 15, 20, 25, 30, 35, 40, 50, 60
10 values of $\theta$ [degrees]: 170, 171, 172, 173, 174, 175, 176, 177, 178, 179
17 values of T2 [s]: 0.01, 0.02, 0.03, 0.04, 0.05, 0.07, 0.1, 0.14, 0.19, 0.27, 0.38, 0.53, 0.74, 1.0, 1.4, 2.0, 2.8
15 values of T1 [s]: 0.05, 0.07, 0.1, 0.14, 0.19, 0.27, 0.38, 0.53, 0.74, 1.0, 1.5, 2.0, 2.8, 4.0, 5.6

A total of 102,000 imaging parameter sets 411 consisting of all combinations of the imaging parameters and the subject parameters described above are constructed, and each signal value is calculated through computer simulation.

In the numerical simulation, a subject model with spins disposed on grid points, the imaging sequence, the imaging parameters, and the apparatus parameters are input to solve Bloch's equations, which are fundamental equations of the magnetic resonance phenomenon, and magnetic resonance signals are output. The subject model is given as a spatial distribution of spins (γ, M0, T1, T2, Sc). Here, γ represents a gyromagnetic ratio, and M0 represents thermal equilibrium magnetization (spin density). By performing image reconstruction of the magnetic resonance signals, images under given conditions can be obtained.

Bloch's equations are first-order linear ordinary differential equations and are represented by Equation (2).

$$\frac{d}{dt}\begin{pmatrix} M_x \\ M_y \\ M_z \end{pmatrix} = \begin{pmatrix} -\frac{1}{T2} & \gamma H & 0 \\ -\gamma H & -\frac{1}{T2} & \gamma H_1 \\ 0 & -\gamma H_1 & -\frac{1}{T1} \end{pmatrix} \begin{pmatrix} M_x \\ M_y \\ M_z \end{pmatrix} + \begin{pmatrix} 0 \\ 0 \\ \frac{M_0}{T1} \end{pmatrix} \quad (2)$$

$$H = B0 + G_x x + G_y y + G_z z + \frac{2\pi \Delta f0}{\gamma}$$

Here, (x, y, z) represents a three-dimensional orthogonal coordinate system, and z is equal to the direction of the static magnetic field (the intensity is B0). Further, (Mx, My, Mz) represents the spins, Gx, Gy, and Gz each represents a gradient magnetic field intensity in a subscripted direction, H1 represents a high-frequency magnetic field intensity, and Δf0 represents the frequency of the rotational coordinate system.

The signal function (fs) 412 is constructed from the signal values obtained through the computer simulation using interpolation. Here, linear interpolation or spline interpolation of about first to third order for the interpolation can be used.

Figure 6:
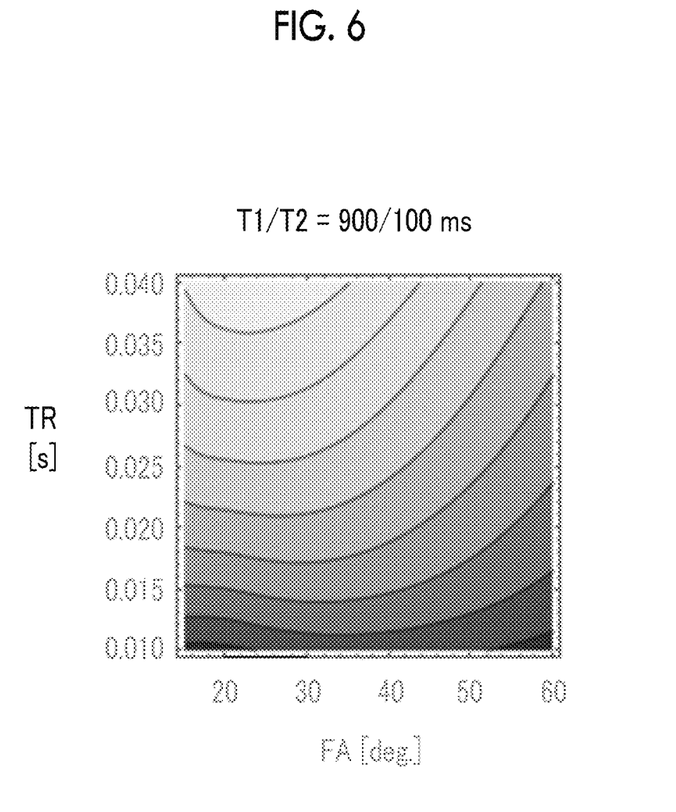
FIG. 6 is a diagram showing a part of a signal function in the embodiment of the present invention.

A part of the intensity of the signal function created as described above is shown in FIG. 6. FIG. 6 shows a case where T1=900 ms, T2=100 ms, and θ=5 degrees, with the horizontal axis and the vertical axis represented as FA and TR, respectively. Once the signal function is created and stored, it can be used repeatedly without the need to create the signal function each time the computed image is captured.

Determination of Imaging Conditions: S301

The imaging condition determination unit 240 determines computed image acquisition imaging parameter sets 413 by using the signal function 412 created as described above. Specifically, the imaging condition determination unit 240 searches for a plurality of imaging conditions (imaging parameter sets) 413 to be used to capture the original image by using the law of error propagation.

Figure 7:
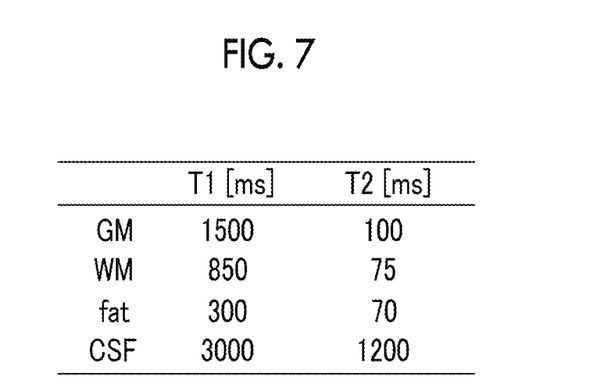
FIG. 7 shows tissues targeted for imaging parameter set optimization and T1 and T2 values thereof in the embodiment of the present invention.

For example, the optimization using the law of error propagation is performed such that estimation errors of each map of T1, T2, B1, and a are minimized for the main tissues of the human head (gray matter GM, white matter WM, fat, and cerebrospinal fluid CSF) as a target. The targeted subject parameters are as shown in FIG. 7. Since the number of unknowns is four (T1, T2, B1, and a), the number of imaging parameter sets is set to six, which is slightly more than the number of unknowns.

Some examples of values of each imaging parameter (FA, TR, and θ) are shown below.
  4 values of FA [degrees]: 10, 20, 30, 40
  4 values of TR [ms]: 10, 20, 30, 40
  20 values of θ: from 160 degrees to 179 degrees (1-degree increments)

In order to increase the SN ratio for quantitative value estimation, TE of the first echo and ΔTE between echoes are usually kept as short as possible to increase the number of multi-echo images. In typical imaging conditions, multi-echo images are captured by setting the shortest TE and ΔTE to, for example, 4.6 ms to fall within TR. In a case where TR is 10 ms, the number of multi-echoes is only one echo under normal imaging conditions, and in a case where TR is 40 ms, the maximum number of multi-echoes is eight echoes (TE of the last echo is 36.8 ms).

Any of these is combined into one set, and among a total of 320 sets of combinations (4×4×20), combinations in which the total of TR values of six sets falls within a predetermined range are set as a search range for searching. The restriction on the total of TR values is to prevent the search range from becoming too extensive and to avoid prolonging the imaging time. Specifically, the total of TR values is set to about 100 ms to 120 ms.

In addition, among the six sets, at least one set of imaging parameters is determined in advance to include a condition in which there is no local decrease in brightness of the blood vessel. This condition can be determined as follows in consideration of the cause of the decrease in brightness of the blood vessel.

One of the main causes of the decrease in brightness of the blood vessel in the gradient echo method is the saturation of blood signals. That is, during imaging, the blood flowing from the lower part of the head to the top is continuously irradiated with RF pulses. Therefore, the magnetization is gradually saturated, the transverse magnetization decreases, and the signal intensity decreases. Accordingly, the brightness of the blood vessel decreases more at the top of the head.

A method of suppressing this signal decrease is to reduce FA and prolong TR. That is, as the imaging condition with a small FA and a long TR, for example, FA=10 and TR=40 are set, and θ is set to, for example, 170. The optimization is performed by always incorporating the condition into the six sets of combinations of imaging conditions.

The determination of the imaging conditions is based on the law of error propagation as described above. However, in this case, the optimization may be performed according to the law of error propagation by incorporating a condition for suppressing a decrease in the blood signal, conditions of the six sets may be determined through the optimization without incorporating the condition for suppressing the decrease in the blood signal and the condition for suppressing the decrease in the blood signal may be added as a condition of a seventh set. In the former case, stable optimization processing can be performed. Further, in the latter case, the weight of the condition for suppressing the decrease in the blood signal increases, which leads to an improved blood signal suppression effect in the quantitative value image.

Further, as different imaging conditions, instead of or in addition to changing the imaging parameters such as TE and FA, an imaging sequence to suppress the decrease in the blood signal may be used. Specifically, in the RF-spoiled GE shown in FIG. 5A, a gradient magnetic field pulse of flow compensation is added between the RF pulse and the echo signal collection (A/D). The addition of the gradient magnetic field pulse of the flow compensation is effective against the decrease in brightness of the blood vessel caused by the turbulent flow. A region where the turbulent flow is likely to occur is a region where the direction of the blood vessel changes rapidly, and in the gradient echo method, a signal tends to decrease in a region where blood flow is turbulent. By adding the gradient magnetic field pulse of the flow compensation, it is possible to ensure high brightness of the blood vessel signal and suppress the decrease in brightness. That is, an imaging condition for suppressing the decrease in the blood signal is obtained.

A pulse sequence example of the RF-spoiled GE to which the gradient magnetic field pulse of the flow compensation is added is shown in FIG. 5B.

In this sequence, a pair of phase-encoding gradient magnetic field pulses having inverted signs are added to the phase-encoding gradient magnetic field pulse 504 of FIG. 5A. As a result, for the phase-encoding gradient magnetic field Gp, a pulse 512 having the same area as the area of the phase-encoding gradient magnetic field pulse 504 but having a different sign, and a pulse 513 having an area twice the area of the phase-encoding gradient magnetic field pulse 504 and the same sign are applied. Further, for the slice gradient magnetic field Gs, a re-phase gradient magnetic field pulse 510 having an area twice the area of the slice direction re-phase gradient magnetic field pulse 503, and a gradient magnetic field pulse 511 having the same area as the area of the re-phase gradient magnetic field pulse 503 but having an inverted sign are applied, and for the readout gradient magnetic field Gr, a gradient magnetic field pulse 514 having the same area as the area of the dephase gradient magnetic field pulse 505 but having a different sign, and a gradient magnetic field pulse 515 having an area twice the area of the dephase gradient magnetic field pulse 505 are applied.

In the pulse sequence of FIG. 5B, the addition of the flow compensation pulse requires TE of the first echo to be longer than the shortest TE described above, but an image having a high blood vessel signal can be obtained.

Measurement of Echo Signal: S302

In a case where a plurality of imaging conditions (combinations of imaging parameters) including the imaging condition for suppressing the decrease in the blood signal are determined as described above, the measurement unit 100 instructs the sequencer 104 to measure the echo signal in accordance with the imaging parameter set determined as the predetermined imaging sequence. Then, the measured echo signal is disposed in the k space to obtain measurement data 414.

Image Reconstruction: S303

The image reconstruction unit 220 performs an inverse Fourier transform on the echo signal (measurement data 414) disposed in the k space by an imaging unit to reconstruct the image. A part (or all) of the reconstructed images can be used as an original image 415 for the blood vessel image synthesis, which will be described below.

Subject Parameter Estimation: S3051

The parameter estimation section 232 uses six reconstructed images generated by the image reconstruction unit 220 and the signal function generated by the signal function generation section 231 to estimate the subject parameters T1, T2, B1, ρ, and the product of the apparatus parameter Sc, which is denoted by a (=ρSc). Specifically, the estimation of the above-described subject parameters and apparatus parameter 416 is performed by fitting a signal value I for each pixel of the reconstructed image to a function f of Equation (3) which is a transformation of Equation (1).

$$I = af(T1, T2, \theta, B1 \times FA, TR, TE)$$

$$a = \rho Sc \quad (3)$$

The function fitting is performed using the least-squares method represented by Equation (4).

$$\chi^2 = \Sigma_{FA, \Delta\theta, TR, TE}\{I(FA, \theta, TR, TE) - af(T1, T2, \theta, B1 \times FA, TR, TE)\} = \min \quad (4)$$

Here, χ represents the sum of residuals between the signal function and the pixel values of the phantom, and I represents the pixel value at (FA, θ, TR, TE).

As described above, an image (quantitative value image) in which the parameter value obtained through the parameter estimation is used as the pixel value is obtained.

Blood Vessel Image Synthesis: S3052

The synthetic image generation unit 250 generates the blood vessel image by synthesizing the image reconstructed by the image reconstruction unit 220 and the quantitative value image. As a method of synthesizing the blood vessel image, it is also possible to use simple addition for each pixel or weighted addition, but in the present embodiment, a technique (the technique described in JP6979151B) of dividing a region and synthesizing each region using a predetermined synthesis function is employed. The procedure of the technique will be described with reference to FIG. 8.

Figure 8:
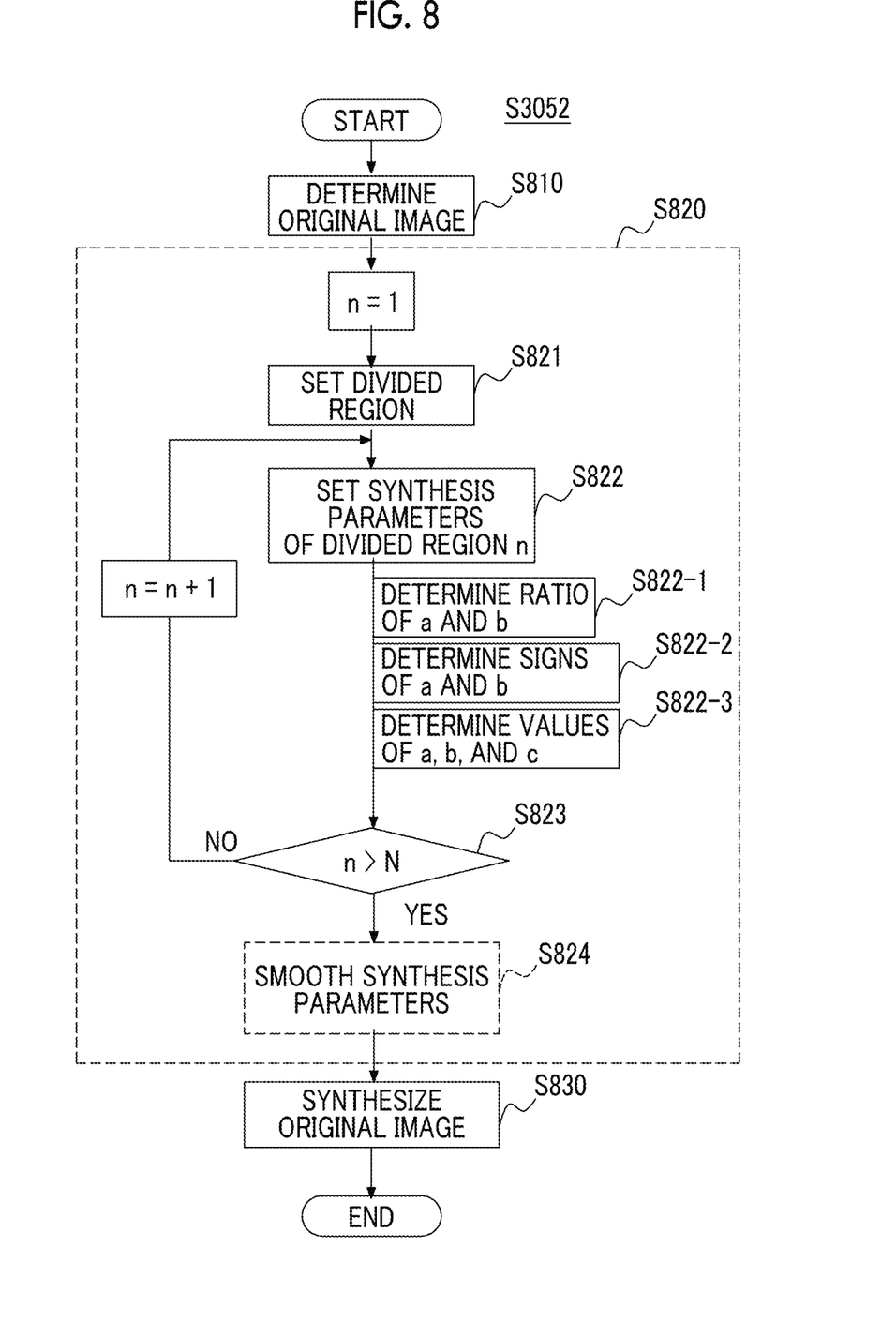
FIG. 8 is a flowchart showing details of a part of processing of FIGS. 5A and 5B.

As shown in FIG. 8, the synthesis of a plurality of images includes step S810 of determining the original image, step S820 of setting the synthesis function and its parameters (synthesis parameters) to be used for the synthesis, and step S830 of synthesizing the images.

Original Image Determination: S810

The image selection section 251 selects two or more types of images, as the original image to be used for the synthesis, from the plurality (here, six sets) of reconstructed images generated by the image reconstruction unit 220, the synthetic image such as a T1-enhanced image or a diffusion-enhanced image generated by the reconstructed image, and the quantitative value image for each parameter generated by the quantitative value image generation unit 230, for example, a T1 image, a T2 image, and a proton density (PD) (ρ) image. In this case, at least one quantitative value image is incorporated into the original image. It is preferable that the two or more types of original images are images having different physical property values (quantitative values) to be emphasized. In such a case, only the quantitative value image may be used as the original image. In addition, as the reconstructed image, an image acquired through imaging using a condition in which the blood flow signal becomes high brightness (for example, a T1-enhanced image or an image acquired using an imaging sequence to which a flow compensation pulse is added) may be used. By selecting an appropriate image and reducing the number of original images, it is possible to reduce the amount of data and shorten the processing time.

Figure 9:
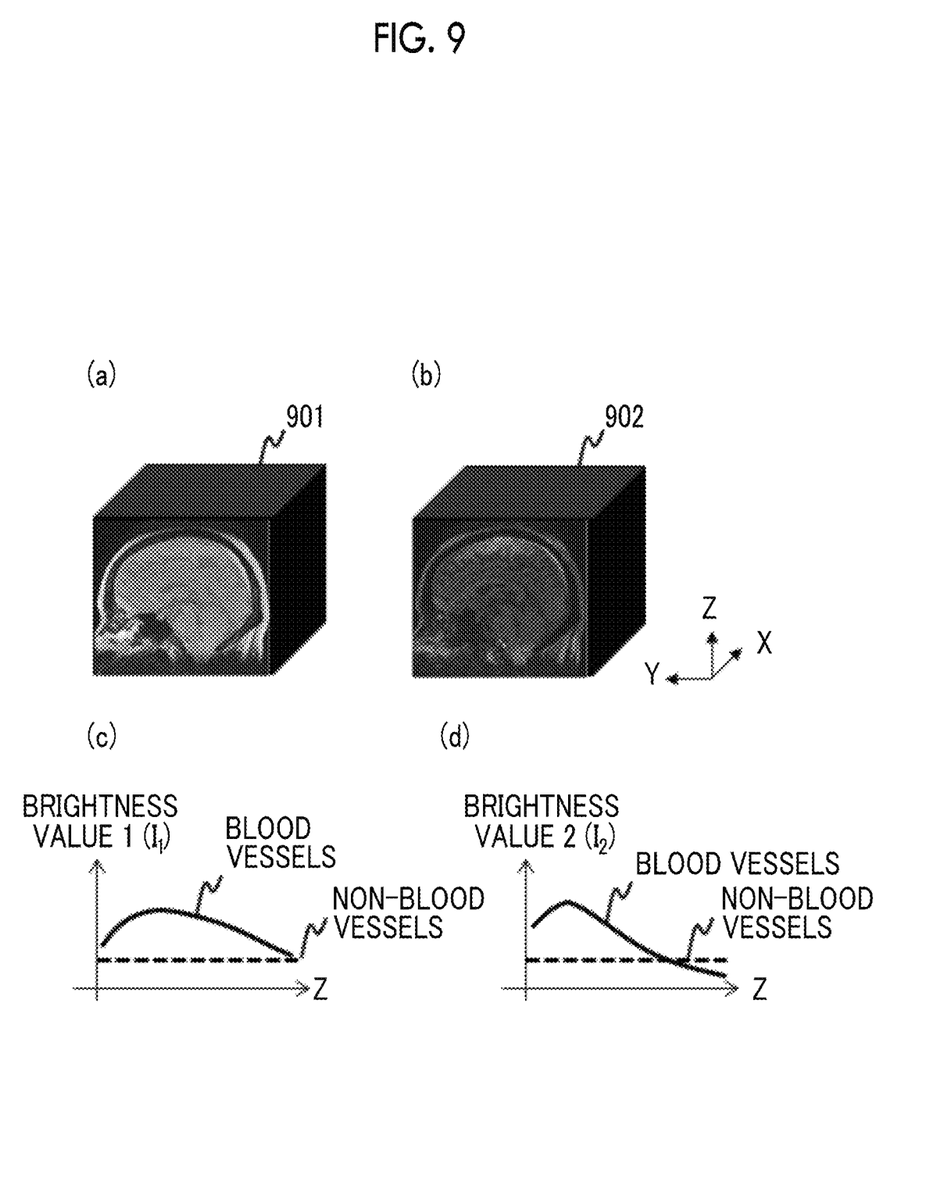
FIG. 9 is a diagram showing an original image for synthesizing a blood vessel image in the embodiment of the present invention.

Here, for example, as shown in FIG. 9, it is assumed that one type of reconstructed image (for example, a PD-enhanced image) 901 and one type of quantitative value image (T1 image) 902 are determined as the original images.

Synthesis Parameter Determination: S820

The synthesis parameter setting section 252 sets parameters (synthesis parameters) of the synthesis function to be used in synthesizing the determined original images.

In a case where the pixel values of the original images 901 and 902 to be synthesized are denoted by $I_1$ and $I_2$, respectively, and the pixel value after the synthesis is denoted by Ic, the synthesis function can generally be described as $Ic = f(I_1, I_2)$. Here, a case where a linear polynomial of Equation (5) is used as an example of the synthesis function will be described.

$$I_c = a \cdot I_1 + b \cdot I_2 + c \quad (5)$$

Here, a and b are coefficients, and c is a constant, which are synthesis parameters set in this step.

The synthesis parameters are set for each region by dividing the image into a plurality of regions. Therefore, the synthesis parameter setting section 252 first specifies a region of interest which is a target of the synthesis parameter calculation, and divides the region of interest into a plurality of regions (S821). After that, the synthesis parameters are set for each of the plurality of divided regions. As shown in (c) and (d) of FIG. 9, it is preferable that the method of division is performed along a direction in which the brightness values of the blood vessels (specific tissues) between the two images 901 and 902 to be synthesized show a difference in the manner of changes. For example, in a case of the blood vessel, it is preferable to divide the blood vessel along the main running direction (along a plane perpendicular to the running direction) of the blood vessel.

Figure 10:
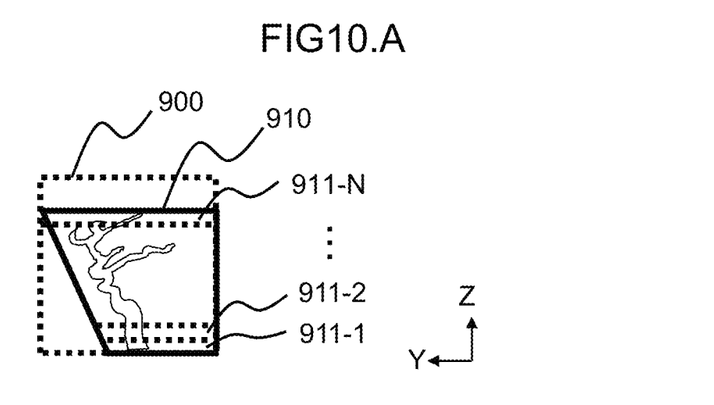
FIGS. 10A to 10C are diagrams illustrating details of synthesis processing in the embodiment of the present invention.

FIG. 10A shows a state of division of the region of interest. In the example of this drawing, a region of interest 910 inside the imaging region set in a human head 900 is divided into N divided regions 911-1 to 911-N, which are parallel to the XY plane. The region of interest 910 is the entire or a part of the imaging region, and is set by setting a predetermined position inside a predetermined imaging region or by receiving an instruction from the user using a user interface. In a case where the imaging regions of the plurality of images are different, the entire or a part of the imaging region common to the plurality of images is used. User instructions may also be accepted for the direction of division and the number of divisions.

At that time, based on pieces of standard data of the pixel values of the blood vessels and the tissues of non-blood vessels, synthesis parameters are set for each divided region such that a condition in which the pixel values of the blood vessels after the synthesis are greater than the pixel values of the non-blood vessels is satisfied and a representative value of pixel values for each divided region is a common value in all the divided regions.

As the pieces of standard data, for example, pieces of data of a plurality of types of images obtained by imaging the predetermined imaging region within a healthy volunteer in advance under the same imaging conditions as the imaging conditions applied to the subject with the measurement unit 100 can be used, and the pieces of data (pre-pixel value data) of pixel values of the blood vessels and the non-blood vessels are used as the pieces of standard data. Information (labels) indicating whether the pixels are the blood vessels or the non-blood vessels is assigned to the pre-pixel value data. The pieces of label information are set, for example, either manually by observing the MRA image acquired by imaging the imaging region of the healthy volunteer using the conventional MRA technique such as a TOF method, or automatically by using binarization processing or the like on the conventional MRA image. The label information is added to the pre-pixel value data.

The synthesis parameter setting section 252 sets the synthesis parameters (a, b, c) for each of the divided regions divided in this way (step S822).

The ranges of possible values of sets of pixel values $I_1$ and $I_2$ for each the pixel labeled as blood vessels and the pixel labeled as non-blood vessels, among the above-described pieces of standard data (pre-pixel value data), are plotted as shown in, for example, a graph in FIG. 10B. A range 921 of the set of pixel values of the blood vessels and a range 922 of the set of pixel values of the non-blood vessels are located at different locations on the plot. In addition, since the range 922 of the set of pixel values of the non-blood vessels includes the distribution of pixels of a plurality of biological tissues such as gray matter and white matter, the range has an elongated elliptical shape.

The synthesis using the synthesis function of Equation (1) described above means that the set of $I_1$ and $I_2$ is projected onto an axis indicated by Ic in FIG. 10B. In that respect, in a case where the synthesis function is applied to $I_1$ and $I_2$ of the pre-pixel value data, the synthesis parameter setting section 252 determines the slope of the axis (Ic) such that the ranges of the possible values of the pixel values Ic of the blood vessels and the tissues of the non-blood vessels do not overlap as much as possible (step S822-1). The slope of the axis is determined by the ratio of the synthesis parameters a and b.

Specifically, first, a vector (a', b') representing the ratio of a and b is determined using Fisher's linear discriminant analysis. (a, b) is determined to be proportional to (a', b').

$$\begin{pmatrix} a' \\ b' \end{pmatrix} = \sum\nolimits^{-1} \cdot \begin{pmatrix} \mu_{1b} - \mu_{1o} \\ \mu_{2b} - \mu_{2o} \end{pmatrix} \quad (6)$$

In Equation (6), $\mu_{1b}$ and $\mu_{2b}$ represent the averages of the pixel values of the blood vessels among the pixel values $I_1$ and $I_2$, respectively, and $\mu_{1o}$ and $\mu_{2o}$ represent the averages of the pixel values of the non-blood vessels among the pixel values $I_1$ and $I_2$, respectively. Further, $\Sigma$ represents a within-class variance represented by Equation (7).

$$\sum = \frac{N_b \sum_b + N_o \sum_o}{N_b + N_o} \quad (7)$$

In Equation (7), Nb and No represent the number of pixels of the blood vessels and the tissues of the non-blood vessels, respectively, and $\Sigma b$ and $\Sigma o$ represent values obtained by dividing the averages of the covariance matrices of the sets of the pixel values $(I_1, I_2)$ in the blood vessels and the tissues of the non-blood vessels, respectively. It is known that the ratio (a', b') calculated using Equation (6) becomes a ratio where, in a case where the length of the vector (a', b') is constant, the ranges of the possible values of the pixel values Ic of the blood vessels and the tissues of the non-blood vessels do not overlap as much as possible, that is, the difference in the pixel values Ic after the synthesis between the blood vessels and the tissues of the non-blood vessels increases.

Next, the signs of a and b are determined such that the average of the pixel values of the blood vessels in the synthetic image (pixel values Ic) is greater than the average of the pixel values of the non-blood vessels (step S822-2). As a result, in the synthesis function, the pixel values of the blood vessels can be made greater than the pixel values of the non-blood vessels. Although a case where a condition for determining the signs of the synthesis parameters a and b is set for each divided region to satisfy a condition in which the pixel values of the blood vessels are greater than the pixel values of the tissues of the non-blood vessels has been described, the condition may be set to satisfy a condition in which the pixel values of the blood vessels are smaller than the pixel values of the tissues of the non-blood vessels, instead.

Next, a, b, and c are determined such that the above-described conditions (that is, the conditions of the ratio and the signs of a and b) are satisfied and the average and the variance of the pixel values Ic of the non-blood vessels are constant (step S822-3). Hereinafter, a case where the average is set to 0 and the variance is set to 1 will be described. First, in a case where a' and b' are substituted into Equation (5) as they are as a and b, the variance Sco of the pixel values Ic in the tissues of the non-blood vessels is represented by Equation (8).

$$S_{co} = (a' \ b') \cdot \sum_o \cdot \begin{pmatrix} a' \\ b' \end{pmatrix} \quad (8)$$

Therefore, it is possible to determine (a, b) such that the variance of the pixel values Ic of the tissues of the non-blood vessels is set to 1 by using Equation (9).

$$\begin{pmatrix} a \\ b \end{pmatrix} = \frac{1}{\sqrt{S_{co}}} \begin{pmatrix} a' \\ b' \end{pmatrix} \quad (9)$$

Further, c is determined using Equation (10) such that the average of the pixel values Ic of the non-blood vessels is 0.

$$c = -(a \ b) \cdot \begin{pmatrix} \mu_{10} \\ \mu_{20} \end{pmatrix} \quad (10)$$

By setting the average to 0 and the variance to 1 in this way, the entire tissues of the non-blood vessels have low brightness (close to 0), and the range of brightness is approximately constant in all the divided regions, so that it is possible to reduce the occurrence of the tissues of the non-blood vessels that may erroneously appear with high brightness as in the blood vessels.

In step S822-3, the average and the variance are made constant across all the divided regions as a condition for determining a, b, and c. However, instead of the average and the variance, similar representative values indicating a range of values of the pixel values Ic, such as a median value and a quartile range, may be made constant (hereinafter, these are collectively referred to as a representative value).

Further, in step S822-3, the synthesis parameters are determined such that the representative value is made constant based on the pre-pixel value data, but the synthesis parameters may be determined such that the representative value (for example, the average and the variance) is made constant based on the image data to be used for the synthesis. Since the number of blood vessels is significantly smaller than that of tissues of the non-blood vessels, the average and variance of the tissues of the non-blood vessels are substantially constant. There is an advantage that an image that is not affected by individual differences such as the proportion of various tissues included in the tissues of the non-blood vessels can be obtained as compared with a case of determination using the pre-pixel value data.

The synthesis parameter setting section 252 repeats the above-described synthesis parameter setting processing (S822-1 to S822-3) from the divided regions 911-1 to 911-N (S823) and calculates the synthesis parameters for each divided region. As shown in (c) and (d) of FIG. 9, the pixel values $I_1$ and $I_2$ of the blood vessels significantly change in the Z direction. In addition, the tissues of the non-blood vessels may also undergo changes in the proportion of included tissues, and the ranges of the pixel values $I_1$ and $I_2$ also change to some extent. Therefore, the synthesis parameters suitable for creating the synthetic image also differ for each divided region depending on the position in the Z direction. It is possible to enhance the accuracy of the synthetic image by determining the synthesis parameters for making the brightness of the blood vessel significantly high compared to the tissues of the non-blood vessels within each divided region and setting the synthesis parameters for each divided region.

Step S830

The synthetic image generation unit 250 generates the synthetic image from the images 901 and 902 of the subject selected in S810 and the synthesis parameters set by the synthesis parameter setting section 252 for each divided region. Specifically, the pixel values $I_1$ and $I_2$ of the same pixel of a plurality of (here, two) images 901 and 902, which are selected from images reconstructed by the image reconstruction unit 220 and images generated by the quantitative value image generation unit 230 for each pixel inside the imaging region, and the synthesis parameters a, b, and c set by the synthesis parameter setting section 252 for the divided region 911-$n$, in which the pixel is included, among the divided regions 911-1 to 911-N are substituted into Equation (1) to obtain the pixel value of the synthetic image at that pixel.

As a result, as shown in FIG. 10C, a synthetic image 930 in which the entire blood vessel can be grasped is obtained. Actually, the synthetic image 930 is a three-dimensional original image, but here, for the sake of illustration, a projection view is shown using a maximum intensity projection (MIP) method.

Figure 11:
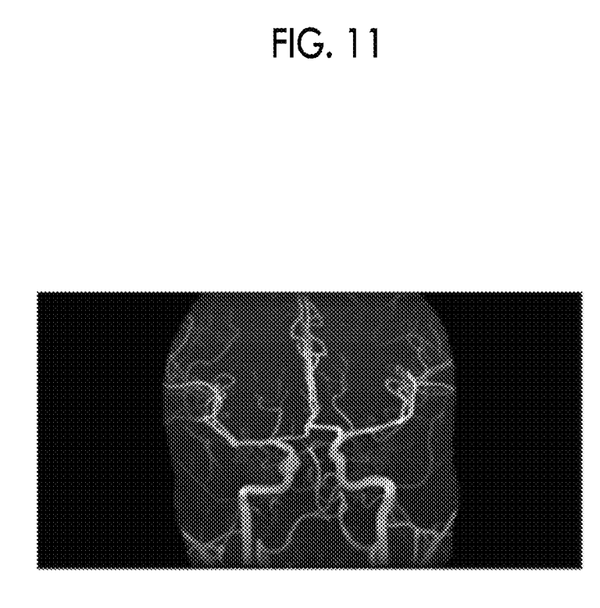
FIG. 11 is a diagram illustrating an image quality improvement effect of the blood vessel image in the embodiment of the present invention.
Figure 12:
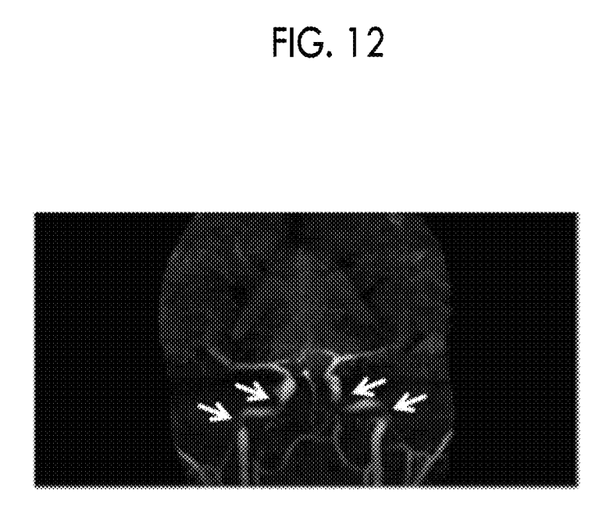
FIG. 12 is a diagram illustrating an image quality improvement effect of the blood vessel image in the embodiment of the present invention.

An example of the blood vessel image of a healthy human head synthesized in this manner is shown in FIG. 11. Further, for comparison, FIG. 12 shows a blood vessel image captured using an imaging parameter set searched for without excluding imaging conditions with poor image quality. In FIG. 12, some parts of the blood vessels (indicated by arrows) and the blood vessels in the vicinity of the top of the head are deficient, while in FIG. 11, such deficiencies are suppressed.

According to the present embodiment, the quantitative value image to be used in generating the synthetic image is constructed from the parameter values estimated using a plurality of images including the reconstructed image acquired under the imaging condition in which the decrease in the blood flow signal is suppressed. Therefore, in the synthesized blood vessel image, a stable synthetic blood vessel image can be obtained without a decrease in brightness of some of blood vessels.

EXPLANATION OF REFERENCES

10: MRI apparatus
100: measurement unit
101: static magnetic field-generating magnet
102: gradient magnetic field coil
103: subject
104: sequencer
105: gradient magnetic field power supply
106: high-frequency magnetic field generator
107: probe
108: receiver
111: display
112: storage medium
200: computer
210: measurement controller
220: image reconstruction unit
230: quantitative value image generation unit
240: imaging condition determination unit
250: synthetic image generation unit

What is claimed is:

1. A magnetic resonance imaging apparatus comprising:
a measurement unit configured to apply a high-frequency magnetic field and a gradient magnetic field to a subject placed in a static magnetic field to measure an echo signal generated from the subject in accordance with an imaging condition and an imaging sequence;
an image reconstruction unit configured to create a reconstructed image from the measured echo signal;
an imaging condition determination unit configured to determine a combination of a plurality of imaging conditions, at least one combination of the plurality of imaging conditions being different from other combinations of the plurality of imaging conditions;
a quantitative value image generation unit configured to generate a quantitative value image in which quantitative values related to the subject are used as pixel values, the quantitative value image being generated by using a plurality of the reconstructed images created by the image reconstruction unit from respective echo signals acquired with the plurality of imaging conditions and a signal function determined by the imaging sequence; and
a synthetic image generation unit configured to synthesize a blood vessel image using an original image including the quantitative value image which was generated by using the plurality of the reconstructed images,
wherein the imaging condition determination unit is configured to incorporate at least one imaging condition in which a local decrease in brightness of a blood vessel is small, into the combination of the plurality of imaging conditions.

2. The magnetic resonance imaging apparatus according to claim 1,
wherein the imaging condition determination unit is configured to incorporate, as one imaging condition in which the local decrease in brightness of the blood vessel is small, a condition with a small flip angle and a long repetition time TR compared to other imaging conditions.

3. The magnetic resonance imaging apparatus according to claim 1,
wherein the imaging condition determination unit is configured to incorporate, as one imaging condition in which the local decrease in brightness of the blood vessel is small, an imaging condition with a long echo time TE to apply a flow suppression pulse.

4. The magnetic resonance imaging apparatus according to claim 3,
wherein the imaging sequence is a gradient echo-based pulse sequence to which the flow suppression pulse is added.

5. The magnetic resonance imaging apparatus according to claim 1,
wherein the imaging condition determination unit is configured to incorporate the imaging condition in which the local decrease in brightness of the blood vessel is small when optimizing the combinations of the plurality of imaging conditions in accordance with a law of error propagation.

6. The magnetic resonance imaging apparatus according to claim 1,
wherein the imaging condition determination unit is configured to add the imaging condition in which the local decrease in brightness of the blood vessel is small after optimizing the combinations of the plurality of imaging conditions in accordance with a law of error propagation.

7. The magnetic resonance imaging apparatus according to claim 1,
wherein the synthetic image generation unit includes an image selection section configured to select an original image to be used for synthesis, and
the image selection section is configured to select one or more types of the quantitative value images as the original image.

8. The magnetic resonance imaging apparatus according to claim 1,
wherein the synthetic image generation unit includes an image selection section configured to select an original image to be used for synthesis, and
the image selection section is configured to select different types of images having different quantitative values or different degrees of quantitative value emphasis.

9. The magnetic resonance imaging apparatus according to claim 1, wherein the quantitative value image generation unit estimates a subject parameter for each pixel using the signal function for each imaging sequence, obtains a subject parameter distribution, and generates the quantitative value image of the subject from the subject parameter distribution.

10. The magnetic resonance imaging apparatus according to claim 1, wherein the quantitative value image generation unit estimates subject parameters by using the plurality of reconstructed images generated by the image reconstruction unit and the signal function, obtains a subject parameter distribution based on the subject parameters, and generates the quantitative value image of the subject from the subject parameter distribution.

11. The magnetic resonance imaging apparatus according to claim 1, wherein the image reconstruction unit generates the plurality of reconstructed images based on the respective echo signals.

12. The magnetic resonance imaging apparatus according to claim 1, wherein the synthetic image generation unit synthesizes the blood vessel image using at least two original image including the quantitative value image and the plurality of the reconstructed images.

13. An image processing device comprising:
a quantitative value image generation unit configured to generate a quantitative value image in which quantitative values related to a subject are used as pixel values, the quantitative value image being generated by using a plurality of reconstructed images reconstructed from respective echo signals acquired by imaging the same subject using a combination of a plurality of imaging conditions, at least one combination of the plurality of imaging conditions being different from other combinations of the plurality of imaging conditions;
an imaging condition determination unit configured to determine the combination of the plurality of imaging conditions required for acquiring the reconstructed images; and
a synthetic image generation unit configured to generate a synthetic image by synthesizing a plurality of images including at least one type of the quantitative value image,
wherein the imaging condition determination unit is configured to incorporate at least one imaging condition in which a local decrease in brightness of a blood vessel is small, into the combination of the plurality of imaging conditions.

14. An image processing method comprising:
- a step of determining a combination of a plurality of imaging conditions using a signal function determined by an imaging sequence in magnetic resonance imaging;
- a step of generating a quantitative value image, in which quantitative values of a subject, which is an imaging target, are used as pixel values, the quantitative value image being generated by using a plurality of reconstructed images acquired through imaging with a plurality of optimized imaging conditions, and the signal function; and
- a step of generating a synthetic image by synthesizing a plurality of images including at least one type of the quantitative value image,
- wherein, in the step of determining the combination of the plurality of imaging conditions, at least one imaging condition in which a local decrease in brightness of a blood vessel is small is incorporated into the combination of the plurality of imaging conditions.

* * * * *